United States Patent [19]
Akhavan-Tafti et al.

[11] Patent Number: 5,484,556
[45] Date of Patent: Jan. 16, 1996

[54] METHODS AND COMPOSITIONS PROVIDING ENHANCED CHEMILUMINESCENCE FROM CHEMILUMINESCENT COMPOUNDS USING DICATIONIC SURFACTANTS

[75] Inventors: M. Hashem Akhavan-Tafti; Zahra Arghavani, both of Sterling Heights, Mich.

[73] Assignee: Lumigen, Inc., Southfield, Mich.

[21] Appl. No.: 442,303

[22] Filed: May 16, 1995

Related U.S. Application Data

[62] Division of Ser. No. 82,091, Jun. 24, 1993, Pat. No. 5,451,347.

[51] Int. Cl.$^6$ .................................................. C09K 3/00
[52] U.S. Cl. ............................................................. 252/700
[58] Field of Search ............................. 252/700; 362/34; 435/4

[56] References Cited

U.S. PATENT DOCUMENTS

| | | |
|---|---|---|
| 3,417,003 | 12/1968 | Ross . |
| 3,925,556 | 12/1975 | Bauman . |
| 4,931,223 | 6/1990 | Bronstein et al. . |
| 4,952,707 | 8/1990 | Edwards et al. . |
| 4,959,182 | 9/1990 | Schaap . |
| 4,978,614 | 12/1990 | Bronstein . |
| 5,004,565 | 4/1991 | Schaap . |
| 5,032,381 | 7/1991 | Bronstein et al. . |

FOREIGN PATENT DOCUMENTS

| | | |
|---|---|---|
| 52636/90 | 10/1990 | Australia . |
| 0087959 | 9/1983 | European Pat. Off. . |
| 352713 | 1/1990 | European Pat. Off. . |
| 2162946 | 2/1986 | United Kingdom . |
| 2233451 | 1/1991 | United Kingdom . |
| 9104668 | 4/1991 | WIPO . |

OTHER PUBLICATIONS

Whitehead et al, Nature, 158 (1983).
G. H. G. Thorpe and L. J. Kricka, Bioluminescence and Chemiluminescence New Perspectives, John Wiley & Sons, Chichester, 199, (1987).
Gundermann, K. D., Bioluminescence and Chemiluminescense, Academic Press, New York, p. 17, (1981).
Metalitza, D. I., et al., J. Biolumin. Chemilumin. 7,21 (1982).
Goto, T. and H. Fukatsu, Tetrahedron Lett., 4299 (1969).
Kricka, L. J., and M. DeLuca, Arch. Biochem. Biophys., 217, 674 (1983).
McCapra, F., Acc. Chem. Res., 9, 201 (1976).
Schaap, A. P., S. Gagnon, J. Amer. Chem. Soc., 104, 3504 (1982).
Wilson, T., Int. Rev. Sci.: Chem., Ser. Two, 9, 265 (1976).
Wilson, T., M. E. Landis, A. L. Baumstark, and P. D. Bartlett, J. Amer. Chem. Soc., 95, 4765 (1973).

(List continued on next page.)

*Primary Examiner*—Philip Tucker
*Attorney, Agent, or Firm*—Ian C. McLeod

[57] ABSTRACT

A dicationic surfactant for enhancing the chemiluminescence of chemiluminescent compounds particularly dioxetanes which are triggerable is described. The surfactant has the formula $$X^-(R_1)_3A^+CH_2-Link-CH_2A^+(R_2)_3X^-$$

wherein A is selected from the group consisting of phosphorus and nitrogen atoms separately or together, wherein X is an anionic counterion and $R_1$ and $R_2$ are selected from the group consisting of unsubstituted and substituted alkyl and aralkyl groups containing 1 to 20 carbon atoms and $R_1$ and $R_2$ can be the same or different, and wherein Link is a carbon chain group selected from the group consisting of dialkylenearyl, aryl, alkylene, alkenylene and alkynylene groups containing 4 to 20 carbon atoms. The surfactants are particularly useful in Western and Southern blot assays.

14 Claims, 3 Drawing Sheets

OTHER PUBLICATIONS

Bartlett, P. D., et al., J. Amer. Chem. Soc. 96, 5557 (1974).
Schaap, A. P., et al., Tetrahedron Lett., 1155 (1987).
Schaap, A. P., et al., Tetrahedron Lett., 935 (1987).
Schaap, A. P., et al., Tetrahedron Lett., 1159 (1987).
Schaap, A. P., Photochem. Photobiol., 47S, 50S (1988).
Shinkai, S., et al., Chem. Lett., 1523 (1981).
Pollard–Knight, D., et al., Anal. Biochem., 185 353 (1990).
Clyne, J. M., et al., J. Biolumin. Chemilumin., 2 357–366 (1989).
Oberfelder, R., Focus 13, 50 (1991).
Sandhu, B. W., et al., BioTechniques 11, 14 (1991).
Ide, S., Kitakyushu Kogyo Koto Senmon Gakko Kenkyu Hokoku, 19, 45–50 (1986) (Abstract).
Maerky, Michael, Helv. Chim. Acta, 64(4), 957–975 (1981) (Abstract).
Yiv, S., et al., J. Colloid Interface Sci., 77(2), 449–455 (1980)).
Laemmli, U. K., Nature (london), 227, 680 (1970) (Abstract).
Domer, F., Schueler, F., Arch. Interm. Pharm., 114, 217–226 (1958).
Horner, L., Schenk, M., Doms, G., Werkst. Korros, 30(6), 413–417 (1979) (Abstract).
Jpn. Kokai Tokyo Koho, JP 58126383 A2 27 Jul. (1983) (Abstract).
Imam, T., Devinsky, F., Lacko, I., Mlynarcik, D., Krasnec, L. Pharmazie, 38(5), 308–310 (1983) (Abstract).
Xiao, X., et al., Anal. Sci. 1, 135–140 (1985).
Ide, S., et al., Anal. Sci. 1, 349–354 (1985).

1 2 3 4 5

1 2 3 4 5

1 2 3

1 2 3

1 2 3

1 2 3

METHODS AND COMPOSITIONS PROVIDING ENHANCED CHEMILUMINESCENCE FROM CHEMILUMINESCENT COMPOUNDS USING DICATIONIC SURFACTANTS

This is a divisional of application Ser. No. 08/082,091 filed on Jun. 24, 1993, now U.S. Pat. No. 5,451,347.

FIELD OF THE INVENTION

The present invention describes a class of dicationic phosphonium and ammonium surfactants which enhance the chemiluminescence produced by the decomposition of chemiluminescent compounds, particularly 1,2-dioxetanes triggered by activating agents such as chemical reagents, including enzymes. Enhancers are substances which increase the amount of chemiluminescence emitted by a chemiluminescent compound. The enhancer may act by increasing the fluorescence quantum yield of the light-emitting species or by increasing the percentage of molecules which produce an electronically excited state product. For the purposes of this invention, enhanced chemiluminescence means that the total light emitted, the maximum light intensity and/or the ratio of light intensity of the reaction compared to the background is greater than that observed in the absence of the enhancer.

BACKGROUND OF THE INVENTION

The detection and quantitation of biological molecules has been accomplished historically with excellent sensitivity by the use of radiolabeled reporter molecules. Recently numerous non-radioactive methods have been developed to avoid the hazards and inconvenience posed by radioactive materials. Methods based on enzyme-linked analytes offer the best sensitivity since the ability to catalytically turn over a substrate to produce a detectable change achieves an amplification. Substrates which generate color, fluorescence or chemiluminescence have been developed, the latter achieving the best sensitivity. In particular, the use of enzyme-triggered chemiluminescent 1,2-dioxetanes has achieved extremely high sensitivity for detection of enzyme-linked analytes.

Further increases in assay sensitivity or speed are needed to expand the range of utility of chemiluminescence-based methods by permitting the detection of analytes present in smaller quantities or reducing the amount of time and/or reagents required to perform the assay. One way to increase the speed and sensitivity of detection in an enzymatic chemiluminescent assay is through the use of reagents which generate light with a higher efficiency or for a greater length of time. This result may be obtained by using chemiluminescent substrates with a higher inherent chemiluminescence efficiency or by the use of enhancer substances which increase the efficiency of light emission.

In addition to increasing light emission, enhancer substances should ideally also be stable under conditions of use. It is desirable that the rate of the chemiluminescence reaction in the presence of the enhancer be relatively rapid as manifested by maximum light intensity and, in an enzyme-initiated reaction, the time required to reach maximal intensity. Further improvement in one or more of these characteristics over compounds known in the art would provide advantages in the application of chemiluminescence in analysis.

PRIOR ART

1. Enhancers of Chemiluminescent Reactions not Involving Dioxetanes.

Various substances are known including 4-substituted phenols, 6-hydroxybenzothiazole and its derivatives and several aromatic amines which enhance the chemiluminescence output from the oxidation of luminol by a peroxide in the presence of a peroxidase enzyme. (European Patent No. 0087959; U. K. Patent Application GB 2162946A; Whitehead et al Nature, 158 (1983)). The nature of the enhancement is not well understood but is thought to be due to the enhancer substance acting as a redox mediator in the enzymatic reaction (G. H. G. Thorpe and L. J. Kricka, Bioluminescence and Chemiluminescence New Perspectives, John Wiley & Sons, Chichester, 199, (1987)). Enhancement is, in any case, not thought to be due to an increase in the fluorescence quantum yield of the excited aminophthalate product nor to an increase in the yield of chemically produced excited states.

2. Enhancement by Surfactants of Chemiluminescence Not Involving Dioxetanes.

Enhancement by surfactants of the chemiluminescent oxidation of luminol (K. D. Gundermann, Bioluminescence and Chemiluminescence, Academic Press, New York, p. 17, (1981); D. I. Metelitza, A. N. Eryomin and V. A. Shibaev, J. Biolumin. Chemilumin., 7, 21 (1982)) have been reported. Chemiluminescence from the chemical oxidation of luciferin was found to increase in the presence of various surfactants due to an increase in the fluorescence quantum yield of the excited state product (T. Goto and H. Fukatsu, Tetrahedron Lett., 4299 (1969)). On the other hand, enzymatic oxidation of luciferin was found to increase in the presence of nonionic surfactants due to an increase in the turnover rate of the enzyme (L. J. Kricka and M. DeLuca, Arch. Biochem. Biophys., 217,674 (1983)). Enhancement of the chemiluminescent oxidation of acridancarboxylic esters by a cationic surfactant was reported to be due to suppression of a competing non-chemiluminescent side reaction (F. McCapra, Acc. Chem. Res., 9, 201 (1976)).

3. Chemical Triggering of Dioxetanes.

The first example in the literature is described in relation to the hydroxy-substituted dioxetane derived from 2,3-diaryl-1,4-dioxene (A. P. Schaap and S. Gagnon, J. Amer. Chem. Soc., 104, 3504 (1982)). However, the hydroxy-substituted dioxetane and any other examples of the dioxetanes derived from the diaryl-1,4-dioxenes are relatively unstable having half-lives at 25° C. of only a few hours. Further, these non-stabilized dioxetanes are destroyed by small quantities of amines (T. Wilson, Int. Rev. Sci.: Chem., Ser. Two, 9, 265 (1976)) and metal ions (T. Wilson, M. E. Landis, A. L. Baumstark, and P. D. Bartlett, J. Amer. Chem. Soc., 95, 4765 (1973); P. D. Bartlett, A. L. Baumstark, and M. E. Landis, J. Amer. Chem. Soc., 96, 5557 (1974), both components used in the aqueous buffers for biological assays.

Examples of the chemical triggering of stabilized dioxetanes were first reported in Schaap U.S. Pat. No. 4,857,652 and a paper (A. P. Schaap, T. S. Chen, R. S. Hanaley, R. DeSilva, and B. P. Giri, Tetrahedron Lett., 1155 (1987)). These dioxetanes exhibit thermal half-lives of years but can be triggered to produce efficient chemiluminescence on demand.

4. Enzymatic Triggering of Dioxetanes.

The first examples of enzymatic triggering of dioxetanes are described in U.S. Pat. No. 4,857,652 and a series of papers (A. P. Schaap, R. S. Handley, and B. P. Giri, Tetrahedron Lett., 935 (1987); A. P. Schaap, M. D. Sandison, and R. S. Handley, Tetrahedron Lett., 1159 (1987) and A. P. Schaap, Photochem. Photobiol., 47S, 50S (1988)). The highly stable adamantyl-substituted dioxetanes bearing a protected phenolic substituent are triggered to decompose with emission of light by the action of an enzyme which removes the protecting group. The phenolic group is subsequently converted at pH >9 to a strongly electron-donating phenoxide anion which dramatically increases the rate of decomposition. As a result, chemiluminescence is emitted at intensities several orders of magnitude above that resulting from slow thermal decomposition. Bronstein PCT 88 00695 also describes enzyme triggerable dioxetanes as does Bronstein U.S. Pat. Nos. 4,978,614, 4,952,707, 5,032,381 and 4,931,223.

5. Enhanced Chemiluminescence From Dioxetanes in the Presence of Surfactants.

A chemiluminescent reaction believed to involve a non-isolable dioxetane was enhanced in micellar solution (S. Shinkai, Y. Ishikawa, O. Manabe, and T. Kunitake, Chem. Lett., 1523 (1981)). The mechanism of enhancement remains unproven but the authors suggested that the yield of excited state products may be increased in the hydrophobic micellar environment as compared to water.

Schaap et al first reported the enhancement of chemiluminescence from the enzyme-triggered decomposition of the stable 1,2-dioxetane, 4-methoxy-4-(3-phosphatephenyl)spiro[1,2-dioxetane-3,2'-adamantane], disodium salt, (LUMIGEN PPD, Lumigen, Inc., Southfield, Mich.) in the presence of water-soluble substances including the ammonium surfactant, cetyltrimethylammonium bromide (CTAB), and a fluorescer. Fluorescent micelles consisting of CTAB and 5-(N-tetradecanoyl)aminofluorescein capture the intermediate hydroxy-substituted dioxetane and lead to a 400-fold increase in the chemiluminescence quantum yield. Enhancement occurs by virtue of an efficient intermolecular energy transfer process from the anionic form of the excited state ester to the fluorescein compound which is held in close proximity and the hydrophobic environment of the surfactant (A. P. Schaap, H. Akhavan and L. J. Romano, Clin. Chem., 35(9), 1863 (1989)).

U.S. Pat. Nos. 4,959,182 and 5,004,565 and European Patent Application No. 89113627.7 describe additional examples of enhancement of chemiluminescence from chemical and enzymatic triggering of stable dioxetanes in the presence of the ammonium surfactant and fluorescers. Fluorescent micelles formed from CTAB and either the fluorescein surfactant described above or 1-hexadecyl-6-hydroxybenzothiazamide enhance the chemiluminescence from the base-triggered decomposition of hydroxy- and acetoxy-substituted dioxetanes. It was also reported that CTAB itself can enhance the chemiluminescence of LUMIGEN PPD (U.S. Pat. Nos. 4,959,182 and 5,004,565). This dioxetane has proven commercially useful for the sensitive detection of alkaline phosphatase. Chemiluminescent detection using LUMI-PHOS® 530, a ready-to-use liquid formulation containing LUMIGEN PPD, has been employed in Southern blotting (D. Pollard-Knight, A. C. Simmonds, A. P. Schaap, H. Akhavan, and M. A. W. Brady, Anal. Biochem., 185, 353 (1990)), a microtiter plate based DNA probe sandwich assay (J. M. Clyne, J. A. Running, H. Akhavan-Tafti, A. P. Schaap, R. S. Stephens, and M. S. Urdea, J. Biolumin. Chemilumin., 2 357–366 (1989)) and Western blotting (R. Oberfelder, Focus, 13, 50 (1991); G. S. Sandhu, B. W. Eckloff, B. C. Kline, BioTechniques 11, 14 (1991)).

U.S. Pat. No. 4,978,614 and U. K. Patent application No. 8914749.0 disclose enhancement of dioxetane chemiluminescence by polymeric quaternary ammonium compounds alone or admixed with fluorescein. Other substances reported to provide marginal enhancement include globular proteins such as bovine albumin, the quaternary ammonium compound benzyldimethylcetylammonium chloride, and nitrogen-containing polymers.

Polyvinylbenzyltrialkylphosphonium salts have been reported to enhance the chemiluminescence generated by the triggered decomposition of stable dioxetanes in pending U.S. application Ser. No. 07/855,537. Also described are copolymers of two or more vinylbenzyltrialkylphosphonium salts and copolymers of one or more vinylbenzyltrialkylphosphonium salts with pendant fluorescer groups attached to one of the monomer constituents.

The prior art does not disclose the use of surfactants with two cationic head groups, such as bis-quaternary ammonium salts, bis-quaternary phosphonium salts or mixed quaternary ammonium-phosphonium salts as chemiluminescence enhancers. Symmetrically substituted bis-trialkylphosphonium and bis-trialkylammonium surfactants, i.e. where all of the alkyl groups are the same are known in the literature. To the best of the inventors' knowledge, mixed bis-alkylphosphonium-bis-triakylammonium surfactants are not reported; unsymmetrically substituted ditrialkylphosphonium and ditrialkylammonium surfactants, i.e. where one set of three alkyl groups differs from the other set are also not reported.

1-(Tri-n-octylphosphoniummethyl)-4-(tri-n-butylphosphoniummethyl)benzene dibromide was used to extract metal ions (Ide, S., Kitakyushu Kogyo Koto Senmon Gakko Kenkyu Hokoku, 19, 45–50 (1986)).

1,4-Bis(tri-n-butylphosphoniummethyl)benzene dibromide was reported in a patent as a bactericide (Legros, Alain, PCT Int. Appl. WO 9104668 A1 18 Apr. 1991)).

1,4-Bis(tri-n-butylphosphoniummethyl)benzene dichloride was used as synthetic precursor in the manufacture of fluorescent whiteners (Maerky, Michael, Helv. Chim. Acta, 64(4), 957–975, (1981)).

1,4-Bis(tri-n-butylphosphoniummethyl)benzene dinitrate, 1,4-bis(tri-n-methylphosphoniummethyl)benzene dinitrate and 1,4-bis(tri-n-methylammoniummethyl)benzene dinitrate were used to electrochemically generate a film of poly-(p-phenylene) S. Ross, U.S. Pat. No. 3,417,003.

1,12-Bis(tributylammonium)dodecane dibromide was reported in a paper describing its physical properties (Yiv, S., Zana, R., J. Colloid Interface Sci., 77 (2), 449–455 (1980)).

1,4-Bis(tri-n-butylammoniummethyl)benzene dibromide was reported in a paper describing its physical properties (Domer, F., Schueler, F., Arch. Interm. Pharm., 114, 217–226 (1958)).

1,4-Bis(tri-n-butylammoniummethyl)benzene dichloride was studied as a corrosion inhibitor (Horner, L., Schenk, M., Doms, G., Werkst. Korros., 30 (6), 413– 417 (1979)).

1,4-Bis(N,N-diethyl-N-octylammoniummethyl)benzene dichloride was reported in a Japanese patent in a process for dyeing fibers (Jpn. Kokai Tokyo Koho, JP 58126383 A2 27 Jul. 1983).

1,4-Bis (N,N-dimethyl-N-decylammoniummethyl)benzene dichloride was reported in a publication as an antimicrobial agent (Imam, T., Devinsky, F., Lacko, I., Mlynarcik, D., Krasnec, L., Pharmazie, 38(5), 308–310 (1983)).

OBJECTS

It is an object of the present invention to provide dicationic phosphonium and ammonium salt surfactant compounds which enhance the chemiluminescence produced by the decomposition of chemiluminescent compounds, particularly 1,2-dioxetanes triggered by activating agents such as chemical reagents, including enzymes. It is an object of the present invention to provide a method and compositions containing a stable 1,2-dioxetane which can be triggered by chemical reagents, including enzymes, in the presence of a dicationic phosphonium and ammonium salt surfactants to generate enhanced chemiluminescence. Further the present invention relates to a method and compositions for the detection of enzymes, and for use in immunoassays and the detection of enzyme-linked nucleic acids, antibodies and antigens such as are generally known in the art. These and other objects will become increasingly apparent by reference to the following description and the drawings.

BRIEF DESCRIPTION OF THE DRAWINGS

FIG. 4A (a reagent of the present invention as used for FIG. 3A) 35 min and 25 min, and FIG. 4B (LUMI-PHOS 530) 60 min and 100 min. Column 1 is 40 ng biotinylated lambda DNA/HindIII fragments. Columns 2 and 3 are 10 and 5 μg EcoRI-restricted mouse genomic DNA, respectively.

DESCRIPTION OF PREFERRED EMBODIMENTS

Figure 1:
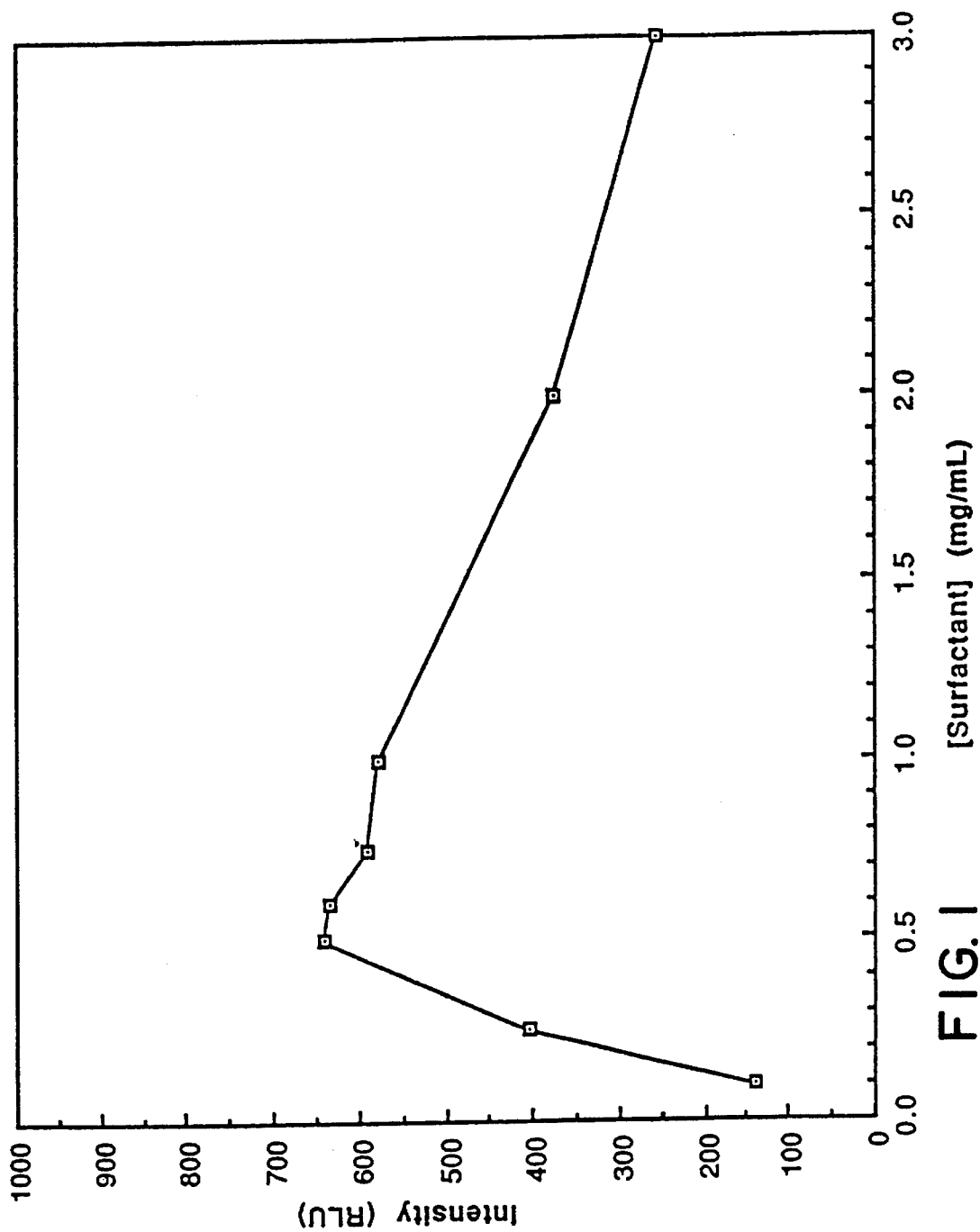
FIG. 1 is a graph of maximum chemiluminescence intensity emitted by 100 μL of a 0.33 mM solution of LUMIGEN PPD in 0.2M 2-methyl-2-amino-1-propanol (221) buffer, pH 9.6 with 0.88 mM $MgCl_2$ and various concentrations of surfactant 12 in the range of 1.0 to 0.01 mg/mL. Chemiluminescence emission was initiated at 37° C. by addition of $9.2 \times 10^{-18}$ mol of calf intestinal alkaline phosphatase. Luminescence values in relative light units (RLU) were measured after two hours in a microwell luminometer and are the average of six wells. Light intensity and signal-to-background are optimum at a surfactant concentration of 0.5–0.6 mg/mL.

The present invention relates to phosphonium and ammonium salt dicationic surfactants of the formula:

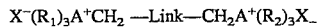

wherein A may be P or N atoms and wherein Link is an organic spacer group containing two or more carbon atoms selected from the group consisting of substituted and unsubstituted aryl, alkyl, alkenyl, alkynyl and wherein Link may contain heteroatoms and wherein $R_1$ and $R_2$ are selected from alkyl or aralkyl containing 1 to 20 carbon atoms and wherein X is halide anion. The $R_1$ and $R_2$ groups on a specific phosphorus or nitrogen atom may all be the same group or may be two different groups or all three may be different. The set of $R_1$ and $R_2$ groups on neighboring phosphorus or nitrogen atoms in the same molecule may be the same set or may be different sets wherein the sets are subject to the description above.

The present invention relates to compositions containing a stable 1,2-dioxetane which can be triggered by an activating agent to generate chemiluminescence in the presence of a dicationic phosphonium or ammonium salt surfactant. Dicationic phosphonium and ammonium salt surfactants useful in practicing the present invention may be of the formula:

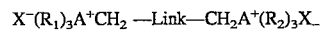

wherein A may be P or N atoms and wherein Link is an organic spacer group containing two or more carbon atoms selected from the group consisting of substituted and unsubstituted aryl, alkyl, alkenyl, alkynyl and wherein Link may contain heteroatoms and wherein $R_1$ and $R_2$ are selected from lower alkyl or aralkyl containing 1 to 20 carbon atoms and wherein X is halide anion. The $R_1$ and $R_2$ groups on a specific phosphorus or nitrogen atom may all be the same group or may be two different groups or all three may be different. The set of $R_1$ and $R_2$ groups on neighboring phosphorus or nitrogen atoms in the same molecule may be the same set or may be different sets wherein the sets are subject to the description above.

The present invention relates to compositions containing a dicationic phosphonium or ammonium salt surfactant in the presence of a stable 1,2-dioxetane which can be triggered by chemical reagents, including enzymes, to generate chemiluminescence. Stable dioxetanes useful in practicing the present invention may be of the formula:

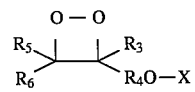

wherein $R_5$ and $R_6$ are organic groups which may be combined together wherein $R_3$ is an organic group which may be combined with P and wherein P represents an aryl group substituted with an X-oxy group which forms an unstable oxide intermediate dioxetane compound when triggered to remove a chemically labile group X by an activating agent selected from acids, bases, salts, enzymes, inorganic and organic catalysts and electron donors. The OX group may be selected from hydroxyl, trialkyl or triarylsilyloxy, inorganic oxyacid salt, phosphate salt, sulfate salt, oxygen pyranoside, aryl and alkyl carboxyl ester. The unstable oxide intermediate dioxetane decomposes and releases electronic energy to form light and two carbonyl containing compounds of the formula

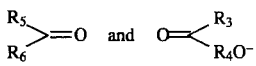

Alternately, stable dioxetanes useful in practicing the present invention may be of the formula:

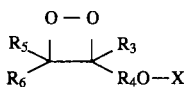

wherein $R_3$ and $R_5$ are organic groups which are combined together, wherein $R_6$ is an organic group and wherein represents an aryl group substituted with an X-oxy group which forms an unstable oxide intermediate dioxetane compound when triggered to remove a chemically labile group X by an activating agent selected from acids, bases, salts, enzymes, inorganic and organic catalysts and electron donors. The OX group may be selected from hydroxyl, trialkyl or triarylsilyloxy, inorganic oxyacid salt, phosphate salt, sulfate salt, oxygen pyranoside, aryl and alkyl carboxyl ester. The unstable oxide intermediate dioxetane decomposes and releases electronic energy to form light and a dicarbonyl compound of the formula

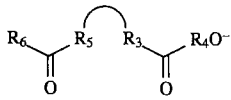

A preferred method of practicing the present invention uses a stable dioxetane of the formula:

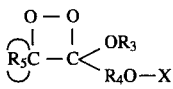

wherein $R_3$ is selected from alkyl or aralkyl containing 1 to 20 carbon atoms and may additionally contain heteroatoms,

is selected from spirofused cyclic and polycyclic organic groups containing 6 to 30 carbon atoms and may additionally contain heteroatoms and wherein is selected from aryl, biaryl, heteroaryl, fused ring polycyclic aryl or heteroaryl groups which can be substituted or unsubstituted and wherein OX is an X-oxy group which forms an unstable oxide intermediate dioxetane compound when triggered to remove a chemically labile group X by an activating agent selected from acids, bases, salts, enzymes, inorganic and organic catalysts and electron donors.

The present invention also relates to compositions in which the amount of chemiluminescence emitted by the dioxetane in the presence of the dicationic phosphonium or ammonium salt surfactant is greater than the amount of light emitted in the absence of the surfactant. The degree of enhancement is dependent upon the nature of the $R_1$ and $R_2$ groups substituting the phosphorus and nitrogen atoms. The degree of enhancement is also dependent on the concentration of surfactant used. Amplification of the chemiluminescence intensity occurs with surfactant concentrations ranging between about 0.001% and about 10%. Surfactants are preferably used at concentrations between about 0.01% and about 0.5%.

The present invention relates to an improved method for generating light which comprises providing a dicationic phosphonium or ammonium salt surfactant in the presence of a stable 1,2-dioxetane of the formula:

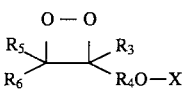

wherein $R_5$ and $R_6$ are organic groups which may be combined together, wherein $R_3$ is an organic group which may be combined with $R_4$ and wherein $R_4$ represents an aryl group substituted with an X-oxy group which forms an unstable oxide intermediate dioxetane compound when triggered to remove a chemically labile group X by an activating agent selected from acids, bases, salts, enzymes, inorganic and organic catalysts and electron donors. The OX group may be selected from hydroxyl, trialkyl or triarylsilyloxy, inorganic oxyacid salt, phosphate salt, sulfate salt, oxygen pyranoside, aryl and alkyl carboxyl ester. The unstable oxide intermediate dioxetane decomposes and releases electronic energy to form light and two carbonyl containing compounds of the formula

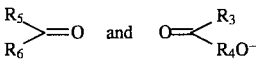

Surfactants useful in practicing the present invention may be of the formula:

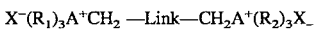

wherein A may be P or N atoms and wherein Link is an organic spacer group containing two or more carbon atoms selected from the group consisting of substituted and unsubstituted aryl, alkyl, alkenyl, alkynyl and wherein Link may contain heteroatoms and wherein $R_1$ and $R_2$ are selected from lower alkyl or aralkyl containing 1 to 20 carbon atoms and wherein X is halide anion. The $R_1$ and $R_2$ groups on a specific phosphorus or nitrogen atom may all be the same group or may be two different groups or all three may be different. The set of $R_1$ and $R_2$ groups on neighboring phosphorus or nitrogen atoms in the same molecule may be the same set or may be different sets wherein the sets are subject to the description above.

It has been found that surfactants such as bis-quaternary ammonium salts, bis-quaternary phosphonium salts or mixed quaternary ammoniumphosphonium salts function effectively as chemiluminescence enhancers. It has also been found unexpectedly that unsymmetrically substituted bis-trialkylphosphonium and bis-trialkylammonium surfactants of the formula:

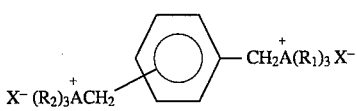

wherein A is P or N and where $R_1$, and $R_2$ are the same or different are superior enhancers of the chemiluminescence resulting from reaction of a stable 1,2-dioxetane.

Preferred dicationic surfactants have alkyl group substituents $R_1$ and $R_2$ which provide a hydrophobic domain for enhancement and a more hydrophilic domain in order to confer sufficient water solubility. As a result the chemiluminescence produced by reaction of a triggerable dioxetane with an activating agent is increased over the amount that would be produced by the same reaction in the absence of the surfactant. At the same time, chemiluminescence produced by the dioxetane in the absence of the activating agent is not significantly enhanced by the surfactant.

The optimum enhancer performance only occurs in compounds of the present invention when certain conditions are met. The groups $R_1$ and $R_2$ must satisfy the opposing requirements of having a hydrophilic site to impart sufficient water solubility and a hydrophobic region to provide chemiluminescence enhancement. These requirements can be met, for example, by choosing a set of smaller alkyl groups for $R_1$ and a set of larger more hydrophobic alkyl groups for $R_2$. Enhancers which meet only one of the two criteria, e.g. symmetrical compounds in which $R_1$ and $R_2$ are the same set are either not effective enhancers or are poorly soluble in water.

The cationic surfactant cetyltrimethylammonium bromide (CTAB) which was used as a chemiluminescence enhancer of triggerable dioxetanes (U.S. Pat. Nos. 4,959,182 and 5,004,565) is thought to effect enhancement by sequestering the emitting species in the relatively hydrophobic core of a micelle. The dicationic trialkylammonium and trialkylphosphonium surfactants of the present invention provide dramatically greater enhancement of chemiluminescence in aqueous environments for triggerable dioxetanes compared to CTAB. The prior art does not suggest that dicationic surfactants could effect efficient chemiluminescence enhancement nor that a specific combination of alkyl substituents with differing properties is required in dicationic trialkylammonium and trialkylphosphonium surfactants for effective chemiluminescence enhancement.

Further, the present invention relates to an improved method for detecting chemiluminescence in aqueous solution from a stable 1,2-dioxetane triggered by an activating agent selected from acids, bases, salts, enzymes, inorganic and organic catalysts and electron donors. The present invention also relates to an improved method for detecting activating agents selected from acids, bases, salts, enzymes, inorganic and organic catalysts and electron donors.

Further the present invention relates to a method and compositions for the detection of enzymes, in immunoassays, e.g. ELISA and the detection of enzyme-linked DNA or A probes. Detection of the light emitted may be readily performed using a luminometer, X-ray film or with a camera and photographic film.

It will be clear to those skilled in the art that surfactants of the present invention may find use as enhancers of other chemiluminescent reactions. Examples of other chemiluminescent reactions which are contemplated include but are not limited to: spontaneous thermal decomposition of dioxetanes of lower stability either pre-formed or generated in situ, in particular, dioxetanes derived from addition of oxygen to enamines, enol ethers and vinyl sulfides;

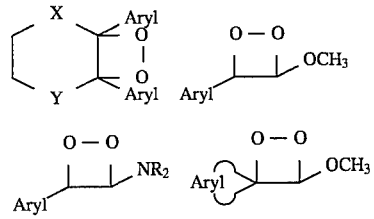

wherein X and Y are selected from N, O and S and wherein Aryl is substituted or unsubstituted phenyl, naphthyl, anthryl, pyrenyl and heteroaryl and especially aryl ring groups substituted with electron-donating substituents such as hydroxy, alkoxy and dialkylamino; chemical or peroxidase-catalyzed oxidation of amino-, alkylamino- and hydroxy-substituted cyclic diacylhydrazides such as:

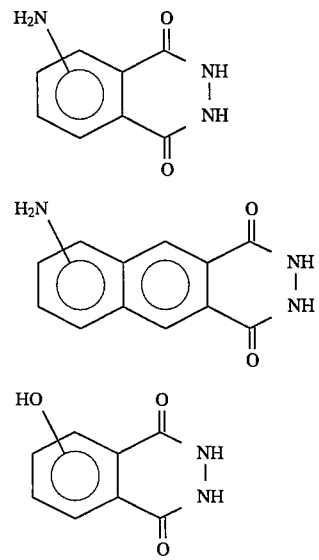

oxidation of bisarylene compounds with alkaline peroxide, the foremost example of which is lucigenin which has the structure:

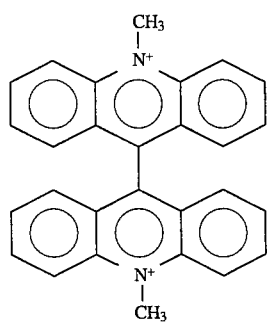

oxidation of acridinium esters, thioesters, and sulfonimides of the general formula:

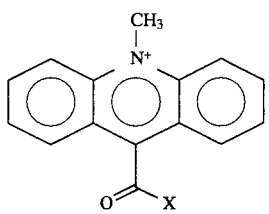

with alkaline peroxide where X is -OAlkyl, -OAryl, -SAlkyl, -SAryl, or -NRSO$_2$R; reaction of hydrogen peroxide with oxalate esters and oxamides of the general formula

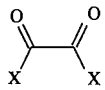

where X is -OAr -NR$_3^+$, -NR$_2$+SO$_2$Ar; illustrative examples include:

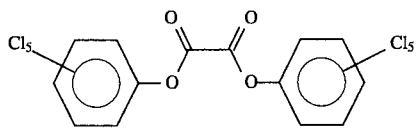

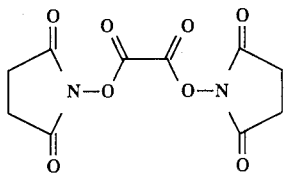

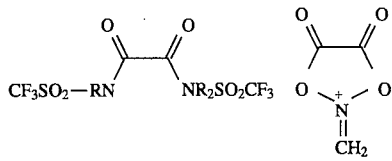

and reaction of luciferins with their respective luciferases, some exemplary luciferins of which include the firefly and *Renilla luciferins*:

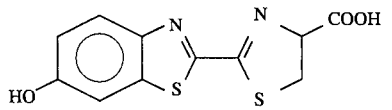

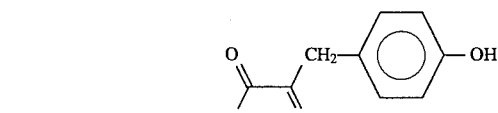

In a preferred method of practicing the present invention a dicationic surfactant is supplied with a stable, triggerable dioxetane wherein the surfactant is of the formula:

wherein the substituents on the benzene ring may be in the ortho-, meta- or para- orientation and wherein A is nitrogen or phosphorus, and wherein R$_1$ and R$_2$ are alkyl or aralkyl containing from 1–20 carbon atoms and wherein X is halide anion. In the preferred method of practicing the present invention, the stable dioxetane is of the formula:

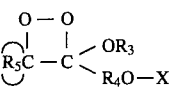

wherein R$_3$ is selected from alkyl or aralkyl containing 1 to 20 carbon atoms and may additionally contain heteroatoms,

is selected from spirofused cyclic and polycyclic organic groups containing 6 to 30 carbon atoms, and may additionally contain heteroatoms and wherein R$_4$ is selected from aryl, biaryl, heteroaryl, fused ring polycyclic aryl or heteroaryl groups which can be substituted or unsubstituted and wherein OX is an X-oxy group which forms an unstable oxide intermediate dioxetane compound when triggered to remove a chemically labile group X by an activating agent selected from acids, bases, salts, enzymes, inorganic and organic catalysts and electron donors. In the most preferred method, R$_3$ is methyl, R$_4$ is meta-phenyl and

is adamantyl or substituted-adamantyl.

In the compositions of the present invention the weight ratio of surfactant to dioxetane is between about 0.1 to 1 and 100 to 1, preferably between about 1 to 1 and 20 to 1. The counterion can be any non-interfering anion such as a halide and nitrate, sulfate, alkylsulfate, alkylsulfonate, arylsulfonate, tetrafluoroborate, perchlorate, alkylcarboxylate and arylcarboxylate.

1. Synthesis of Phosphonium and Ammonium Salt Surfactants.

The enhancers in the first group were made via the general reaction:

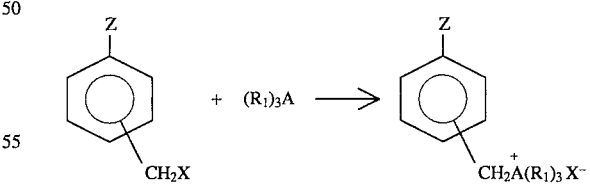

where A=N or P, Z=CH$_2$X, CH$_2$P(R$_2$)$_3$+X$^-$ or CH$_2$N(R$_2$)$_3$+X$^-$ and X=Cl, Br or I.

2-(Chloromethyl)benzyltriethylphosphonium chloride (1).

To a mixture of α,α'-dichloro-o-xylene (15.0 g, 86.0 mmol) in toluene (200 ml) was added triethylphosphine (6.3 ml, 43.0 mmol) under argon gas. The reaction mixture was stirred for several days at room temperature under argon after which time the triethylphosphonium chloride salt had crystallized out of solution. The crystals were filtered and washed with toluene (3×50 mL) and pentane (3×50 mL) and dried: $^1$H NMR (CDCl$_3$) δ 1.15–1.26 (dt, 9), 2.58–2.69 (m, 6H), 4.39–4.44 (d, 2H), 4.87 (s, 2H), 7.31–7.34 (dd, 2H), 7.43–7.46 (dd, 1H), 7.50–7.54 (m, 1H).

2-(Chloromethyl)benzyltri-n-butylphosphonium chloride (2).

A mixture of tri-n-butylphosphine (18.9 g, 103.8 mmol) in toluene (50 mL) was added dropwise to a mixture of α,α'-dichloro-o-xylene (7.0 g, 34.6 mmol) in toluene (200 mL) under argon gas. The reaction mixture was allowed to stir for several days at room temperature under argon, at which time TLC examination showed completion of reaction. Toluene was removed under reduced pressure to give an oily residue. The above oily residue was washed with toluene/hexane (50/50 (v/v), 4×100 mL), and then dried to give a colorless oil. $^1$H NMR (CDCl$_3$) δ0.89 (t, 9H), 1.43 (m, 12H), 2.52 (m, 6H), 4.41 (d, 2H), 4.88 (s, 2H), 7.33 (m, 2H), 7.4 5 (m, 1H), 7.52 (m, 1H).

3-(Chloromethyl)benzyltri-n-butylphosphonium chloride (3).

A mixture of tri-n-butylphosphine (18.9 g, 103.8 mmol) in toluene (50 mL) was added dropwise to a mixture of α,α'-dichloro-m-xylene (7.0 g, 34.6 mmol) in toluene (200 mL) under argon gas. The reaction mixture was allowed to stir for several days at room temperature under argon, after which time the tri-n-butylphosphonium chloride salt had crystallized out of solution and TLC examination showed completion of reaction. The white crystals were filtered and washed several times with toluene and hexanes, and then dried. $^1$H NMR (CDCl$_3$) δ0.93 (t, 9H), 1.45 (m, 12H), 2.41 (m, 6H), 4.40 (d, 2H), 4.57 (s, 2H), 7.36 (m, 2H), 7.42 (d, 2H).

4-(Chloromethyl)benzyltri-n-butylphosphonium chloride (4).

A mixture of tri-n-butylphosphine (7 g, 34.6 mmol, leq.) in toluene (50 mL) was added dropwise to a mixture of α,α'-dichloro-p-xylene (12.1 g, 69.8 mmol, 2 eq.) in toluene (200 mL) under argon gas. The reaction mixture was allowed to stir for 12 hours at room temperature under argon, after which time the tri-n-butylphosphonium chloride salt had crystallized out of solution. The crystals were filtered and washed several times with toluene and hexanes, then air dried: $^1$H NMR (CDCl$_3$) δ 0.92 (t, 9H), 1.44 (m, 12H), 2.39 (m, 6H), 4.35–4.40 (d, 2H), 4.56 (s, 2H), 7.36–7.39 (d, 2H), 7.47–7.51 (dd, 2H).

4-(Bromomethyl)benzyltri-n-butylphosphonium bromide (5).

A mixture of tri-n-butylphosphine (5.7 g, 28.4 mmol) in toluene (50 mL) was added dropwise to a mixture of α,α'-dibromo-p-xylene (15 g, 56.8 mmol, 2 eq.) in 200 mL of toluene under argon gas. The reaction mixture was allowed to stir for several days at room temperature under argon, after which time the tri-n-butylphosphonium bromide salt had crystallized out of solution. The crystals were filtered and washed three times each with 50 mL portions toluene and hexanes, then air dried: $^1$H NMR (CDCl$_3$) δ0.93 (t, 9H), 1.45 (m, 12H), 2.40 (m, 6H), 4.33–4.37 (d, 2H), 4.47 (s, 2H), 7.37–7.40 (d, 2H), 7.46–7.49 (dd, 2H).

1,2-Bis(tri-n-butylphosphoniummethyl)benzene dichloride (6).

To a mixture of α,α'-dichloro-o-xylene (2 g, 11.0 mmol) in anhydrous DMF (30 mL) was added tri-n-butylphosphine (5.6 g, 28.0 mmol) under argon gas. The reaction mixture was stirred under argon at room temperature for several days, after which time TLC examination showed completion of reaction. DMF was removed under reduced pressure to give an oily residue. The oily residue was washed sequentially with hexane (4× 80 mL), toluene (2×50 mL) and again with hexane (2× 50 mL) and dried: $^1$H NMR (CDCl$_3$) δ0.92 (t, 18H), 1.4 6 (m, 24H), 2.52 (m, 12H), 4.68–4.73 (d, 4H), 7.40–7.41 (d, 2H), 7.68–7.69 (d, 2H).

1,3-Bis(tri-n-butylphosphoniummethyl)benzene dichloride (7).

To a mixture of α,α'-dichloro-m-xylene (12 g, 69.2 mmol) in anhydrous DMF (50 mL) was added tri-n-butylphosphine (28 g, 138.6 mmol) under argon gas. The reaction mixture was stirred under argon at room temperature for several days after which time TLC examination showed completion of reaction. DMF was removed under reduced pressure to give an oily residue. The above oily residue was washed with toluene/hexane (50/50 (v/v); 4×100 mL), and then dried to give white crystals. $^1$H NMR (CDCl$_3$) δ0.93 (t, 18H), 1.4 8 (m, 24H), 2.39 (m, 12H), 4.35 (d, 4H), 7.38 (t, 2H), 7.55 (d, 1H), 8.24 (s, 1H).

1,4-Bis( tri-n-butylphosphoniummethyl)benzene dichloride (8).

To a mixture of 4-(chloromethyl)benzyl tri-n-butylphosphonium chloride (2.5 g, 6.6 mmol) in anhydrous DMF (30 mL) was added tri-n-butylphosphine (2 g, 9.9 mmol) under argon gas. The above reaction mixture was stirred under argon at room temperature for several days after which time the tri-n-butylphosphonium chloride salt had crystallized out of solution. The above crystals were filtered and washed with hexanes (3×30 mL) and then dried to give 1,4-bis(tri-n-butylphosphoniummethyl) benzene dichloride as white crystals: $^1$H NMR (CD$_3$OD) δ0.98 (t, 18H), 1.51 (m, 24H), 2.21 (m, 12H), 3.80–3.85 (d, 4H), 7.45 (s, 4H).

1-Tri-n-octylphosphoniummethyl)-2-(triethylphosphoniummethyl)benzene dichloride (9).

To a mixture of 2 -(chloromethyl)benzyltriethylphosphonium chloride (5.0 g, 17.1 mmol) in DMF at room temperature under argon was added tri-n-octylphosphine (9.45 g, 26.0 mmol). The react ion mixture was stirred for several days under argon after which time TLC examination showed completion of the; reaction. DMF was removed under reduced pressure to give an oily residue. The residue was washed several times with toluene and hexane and then dried to give a colorless oil. $^1$H NMR (CDCl$_3$) δ0.87 (t, 9H), 1.14–1.43 (m, 45H), 2.4[(m, 6H), 2.62– 2.69 (m, 6H), 4.64–4.74 (t, 4H), 7.37–7.42 (m, 2H), 7.53–7.55 (m, H), 7.84–7.86 (m, H) .

1-(Tri-n-octylphosphoniummethyl)-2-(tri-n-butylphosphoniummethyl)benzene dichloride (10).

To a mixture of 2-(chloromethyl)benzyl tri-n-butylphosphonium chloride (4 g, 11.0 mmol) in DMF at room temperature, under argon was added tri-n-octylphosphine (5.7 g, 15.4 mmol). The above reaction mixture was allowed to stir for several days at room temperature under argon, at which time TLC examination showed completion of reaction. DMF was removed under reduced pressure to give an oily residue. The above residue was washed several times with pentane and a mixture of toluene/pentane (v/v, 20/80). Then it was dried under reduced pressure to give a colorless oil. $^1$H NMR (CDCl$_3$) δ0.88 (t, 9H), 0.93 (t, 9H), 1.25 (br s, 24H), 1.43 (m, 24H), 2.53 (m, 12H), 4.67–4.69 (d, 2H), 4.73–4.75 (d, 2H), 7.40 (t, 2H), 7.71 (m, 2H).

1-(Tri-n-octylphosphoniummethyl)-3-(tri-n-butylphosphoniummethyl)benzene dichloride (11).

To a mixture of 3-(chloromethyl)benzyl tri-n-butylphosphonium chloride (2.2 g, 5.8 mmol) in DMF at room temperature, under argon was added tri-n-octylphosphine (3.2 g, 8.7 mmol). The reaction mixture was allowed to stir for several days at room temperature under argon, at which time TLC examination showed completion of reaction.

DMF was removed under reduced pressure to give an oily residue. The colorless oil was washed several times with pentane and a mixture of toluene/pentane (v/v, 30/70), and then dried. $^1$H NMR (CDCl$_3$) δ0.88 (t, 9H), 0.93 (t, 9H), 1.25 (br s, 24H), 1.44 (m, 24H), 2.39 (m, 12H), 4.33–4.38 (d, 4H), 7.38 (t, 1H), 7.5–7.6 (dd, 2H), 8.24 (s, 1H).

1-(Tri-n-octylphosphoniummethyl),-4-(tri-n-butylphosphoniummethyl)benzene dichloride (12).

To a mixture of 4-(chloromethyl)benzyl tri-n-butylphosphonium chloride (3 g, 7.9 mmol) in DMF at room temperature, under argon was added tri-n-octylphosphine (4.39 g, 12 mmol). The reaction mixture was allowed to stir for several days, after which time TLC examination showed completion of reaction. DMF was removed under reduced pressure. The residue was washed with hexanes and toluene several times and, then dried to give 1-(tri-n-octylphosphoniummethyl)- 4-(tri-n-butylphosphoniummethyl)benzene dichloride as white crystals: $^1$H NMR (CDCl$_3$) δ0.84 (t, 9H), 0.89 (t, 9H), 1.22 (br s, 24H), 1.41 (m, 24H), 2.34 (m, 12H), 4.35–4.40 (d, 4H), 7.58 (s, 4H); $^{13}$C NMR (CDCl$_3$) δ13.34, 13.94, 18.33, 18.62, 18.92, 19.21, 21.76, 21.81, 23.58, 23.64, 23.78, 23.98, 26.10, 26.65, 28.86, 30.68, 30.88, 31.53, 129.22, 131.22; $^{-}$P NMR (D$_2$O) δ31.10, 31.94.

1-(Tri-n-octylphosphoniummethyl)-4-tri-n-butylphosphoniummethyl)benzene dibromide (13).

To a mixture of 4-(bromomethyl)benzyl tri-n-butylphosphonium bromide (5 g, 11 mmol)in DMF at room temperature, under argon was added tri-n-octylphosphine (4.97 g, 13 mmol). The reaction mixture was allowed to stir for several days, at which time TLC examination showed completion of reaction. DMF was removed under reduced pressure. The residue was dissolve in toluene and pentane added to induce crystallization. The resulting crystals were filtered, washed with pentane and dried to give 1-(tri-n-octylphosphoniummethyl)- 4-(tri-n-butylphosphoniummethyl)benzene dibromide as white crystals: $^1$H NMR (CDCl$_3$) δ0.88 (t, 9H), 0.92 (t, 9H), 1.26 (br s, 24H), 1.45 (m, 24H), 2.35 (m, 12H), 4.36 4.41 (d, 4H), 7.60 ( s, 4H).

1,4-Bis(tri-n-octylphosphoniummethyl)benzene dibromide (14).

To a mixture of α,α'-dibromo-p-xylene (5 g, 18.9 mmol) in anhydrous DMF (50 mL) was added tri-n-octylphosphine (21 g, 56.7 mmol) under argon gas. The reaction mixture was stirred under argon in an oil bath at 80° C. for 12 h, at which time TLC examination showed completion of reaction. DMF was removed under reduced pressure to give an oily residue. The residue was dissolved in a mixture of toluene/hexane (30/70 (v/v), 200 mL) and crystallized at −5° C. The crystals were filtered and washed several times with hexanes, and then dried. $^1$H NMR (CDCl$_3$) δ0.85 (t, 18H), 1.32 (br d, 72H), 2.33 (t, 12H), 4.37 (d, 4H), 7.56 (s, 4H).

1,4-Bis(tri-n-octylphosphoniummethyl)benzene dichloride (15).

To a mixture of α,α'-dichloro-p-xylene (5 g, 28.6 mmol) in anhydrous DMF (50 mL) was added tri-n-octylphosphine (26 g, 70 mmol) under argon gas. The reaction mixture was stirred under argon in an oil bath at 80° C. for 12 hr, at which time TLC examination showed completion of reaction. DMF was removed under reduced pressure to give an oily residue. The residue was dissolved in hexane (200 mL) and crystallized at −5° C. The crystals were filtered and washed several times with hexanes, and then dried. $^1$H NMR (CDCl$_3$) δ0.88 (br s, 18H), 1.26 and 1.44 (2 br s, 72H), 2.36 (br s, 12H), 4.37 (d, 4H), 7.58 (s, 4H).

4-(Chloromethyl)benzyltri-n-butylammonium chloride (16). A mixture of tri-n-butylamine (6 g, 32.2 mmol) and α,α'-dichloro-p-xylene (8.0 g, 46.0 mmol) in methanol (50 mL) was refluxed for 15 h after which time TLC examination showed completion of the reaction. Methanol was removed under reduced pressure to give an oily residue. The colorless oil was washed several times with toluene and hexane and then dried. The product obtained was used without further purification.

4-(Bromomethyl)benzyltri-n-butylammonium bromide (17).

To a mixture of α,α'-dibromo-p-xylene (7.0 g, 26.5 mmol) in toluene (200 m L) was added tri-n-butylamine (3.4 3 g, 18.6 mmol) under argon gas. The reaction mixture was stirred for several days at room temperature under argon at which time the tri-n-butylammonium salt had crystallized out of solution. The crystals were filtered and washed with toluene (3×50 mL) and hexanes (3×50 mL) and dried: $^1$H NMR (CDCl$_3$) δ0.97 (t, 9H), 1.39 (m, 6H), 1.76 (m, 6H), 3.32 (m, 6H), 4.4 7 (s, 2H), 4.96 (s, 2H), 7.4 2–7.59 (dd, 4H).

4-(Iodomethyl)benzyltri-n-butylammonium iodide (18).

To a mixture of α,α'-dichloro-p-xylene (50 g, 28.6 mmol) and sodium iodide (8.6 g, 57 mmol) in acetone (100 mL) was added tri-n-butylamine (3.7 g, 20.0 mmol). The reaction mixture was stirred at room temperature under argon for several days after which time TLC examination showed completion of the reaction. The reaction mixture was filtered and the solvent was removed under reduced pressure to give an oily residue. The residue was washed with pentane several times and dried to give a yellow solid. The product was used without further purification.

1-(Tri-n-octylphosphoniummethyl)-4-tri-n-butylammoniummethyl)benzene dichloride (19).

To a mixture of crude 4-(chloromethyl)benzyl tri-n-butylammonium chloride (2.5 g, 7.0 mmol) in DMF at room temperature under argon was added tri-n-octylphosphine (3.8 g, 11.0 mmol). The reaction mixture was stirred for several days after which time TLC examination showed completion of the reaction. DMF was removed under reduced pressure The residue was washed with hexanes and toluene several times and dried: $^1$H NMR (CDCl$_3$) δ0.87 (t, 9H), 0.99 (t, 9H), 1.25–1.78 (m, 8H), 2.35 (m, 6H), 3.30 (m, 6H), 4.47–4.52 (d, 2H), 5.10 (s, 2H), 7.68 ( s, 4H).

1-(Tri-n-octylammoniummethyl)-4-(tri-n-butylphosphoniummethyl)benzene dibromide (20 ).

To a mixture of 4-(bromomethyl)benzyltri-n-butylphosphonium bromide (2.5 g, 5.3 mmol) in acetonitrile at room temperature under argon was added tri-n-octylamine (2.85 g, 8 mmol ). The reaction mixture was stirred for several days at which time TLC examination showed completion of reaction. Acetonitrile was removed under reduced pressure. The oily residue was washed with pentane several times and then dried to give a white solid: $^1$H NMR (CDCl$_3$) δ0.88 (t, 9H), 0.94 (t, 9H), 1.27–1.50 (3 br s, 42H), 1.81 (m, 6H), 2.39 (m, 6H), 3.26 (m, 6H), 4.53–4.58 ( d, 2H), 5.09 (s, 2H), 7.62–7.67 (dd, 4H).

1-(Tri-n-octylammoniummethyl)-4-(tri-n-butylammoniummethyl)benzene dibromide (2L).

To a mixture of 4-bromomethyl)benzyltri-n-butylammonium bromide (2.43 g, 5.4 mmol) in DMF at r.t., under argon was added tri-n-octylamine (2.0 g, 5.4 mmol). The reaction mixture was stirred for several days at which time TLC examination showed completion of the reaction. DMF was removed under reduced pressure. The oily residue was washed with toluene and pentane several times and then dried to give a white solid: $^1$H NMR (CDCl$_3$) δ0.87 (t, 9H), 0.99 (t, 9H), 1.26–1.44 (m, 36H), 1.80 (m, 12H), 3.27–3.35 (m, 12H), 5.17 (s, 4H), 7.72 (s, 4H).

1-(Tri-n-octylammoniummethyl)-4-(tri-n-butylammoniummethyl)benzene diiodide (22).

To a mixture of 4-(iodomethyl)benzyltri-n-butylammonium iodide (2.44 g, 4.5 mmol) in acetone (50 mL) at room temperature under argon was added tri-n-octylamine (1.6 g, 4.5 mmol). The reaction mixture was stirred for several days after which time TLC examination showed completion of the reaction. Pentane was added to the reaction mixture (150 mL), which led to the formation of white crystals. The crystals were filtered and washed with pentane several times and then dried: $^1$H NMR (CDCl$_3$) δ0.87 (t, 9H), 0.99 (t, 9H), 1.26–1.44 (m, 36H), 1.82 (m, 12H), 3.29–3.35 (m, 12H), 5.23 (s, 4H), 7.72 (s, 4H).

1-(Tridodecylammoniummethyl)-4-(tri-n-butylammoniummethyl)benzene diiodide (23).

To a mixture of crude 4-(iodomethyl)benzyltri-n-butylammonium iodide (3.45 g, 6.3 mmol) in acetone (50 mL) was added tridodecylamine (2.3 g, 6.3 mmol). The reaction mixture was stirred for several days at room temperature under argon after which time TLC examination showed completion of the reaction. Pentane (150 ml) was added to the reaction mixture which led to the formation of an oily residue on the bottom of the flask. The oily residue was washed with hexane several times and then dried: $^1$H NMR (CDCl$_3$) δ0.88 (t, 9H), 1.00 (t, 9H), 1.25–1.34 (m, 60H), 1.82 (m, 12H), 3.33 (m, 12H), 20 (s, 4H), 7.72 (s, 4H).

The enhancers in the second group were made via the general reaction:

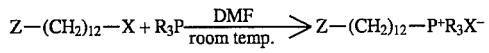

where Z=CH$_2$X, CH$_2$P+R$_3$X- or CH$_2$N+R$_3$X- and X=Cl, Br or I.

1-Bromo-12-(tri-n-butylphoshonium)dodecane bromide (24).

To a mixture of 1,12-dibromododecane (10 g, 30.0 mmol) in toluene (70 mL) was added tri-n-butylphosphine (1 g, 5.0 mmol) under argon gas. The above reaction mixture was stirred under argon at room temperature for several days, at which time TLC examination showed completion of reaction. Toluene was removed under reduced pressure to give an oily residue. The residue was washed several times with pentane and hexane, washed two times with a mixture of toluene/hexane (10/90 (v/v), 25 mL), and then dried under reduced pressure to give a colorless oil. $^1$H NMR (CDCl$_3$) δ0.96 (t, 9H), 1.24 and 1.50 (2 br s, 30H), 1.83 (m, 2H), 2.4 3 (m, 8H), 3.39 (m, 2H).

1,12-Bis(tri-n-butylphosphonium)dodecane dibromide (25).

To a mixture of 1,12-dibromododecane (5g, 15.0 mmol) in anhydrous DMF (15 mL) was added tri-n-butylphosphine (8 g, 39.0 mmol) under argon gas. The reaction mixture was stirred under argon at room temperature for several days, at which time TLC examination showed completion of reaction. DMF was removed under reduced pressure to give an oily residue. The residue was washed several times with toluene and hexane, then dissolved in a mixture of toluene/hexane (30/70 (v/v), 200 mL) and crystallized at −5° C. The crystals were filtered, washed several times with hexanes and dried. $^1$H NMR (CDCl$_3$) δ0.97 (t, 18H), 1.32 and 1.53 (2 br s, 44H), 2.4 3 (m, 16H).

1-(Tri-n-butylphosphonium)-12-(tri-n-octylphosphonium)dodecane dibromide (26).

To a mixture of 1-bromo-12-(tri-n-butylphosphonium)dodecane bromide (2 g, 3.8 mmol) in anhydrous DMF (15 mL) was added tri-n-octylphosphine (2 g, 5.7 mmol) under argon gas. The reaction mixture was stirred under argon at room temperature for several days, at which time TLC examination showed completion of reaction. DMF was removed under reduced pressure to give an oily residue. The residue was washed several times with pentane and a mixture of toluene/pentane (v/v, 20/80). Then it was dried under reduced pressure o give a colorless oil: $^1$H NMR (CDCl$_3$) δ0.87 (t, 9H), 0.97 (t, 9H), 1.26 (br s, 36H), 1.53 (m, 32H), 2.43 (m, 16H). 1,12-Bis(tri-n-octylphosphonium)dodecane dibromide (27).

To a mixture of 1,12-dibromododecane (5 g, 15.0 mmol) in anhydrous DMF (15 mL) was added tri-n-octylphosphine (15 g, 39.0 mmol) under argon gas. The reaction mixture was stirred under argon at room temperature for several days, at which time TLC examination showed completion of reaction. DMF was removed under reduced pressure to give an oily residue. The residue was washed several times with toluene and hexane, dissolved in a mixture of toluene/hexane (30/70 (v/v), 200 mL) and crystallized at −5° C. The crystals were filtered, washed several times with hexanes and dried. $^1$H NMR (CDCl$_3$) δ0.83 (t, 18H), 1.22 and 1.46 (2 br s, 92H), 2.38 (m, 16H).

The structures of 1 through 27 are as follows:

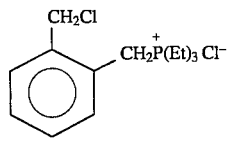

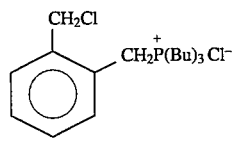

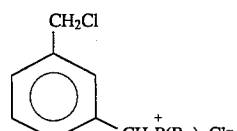

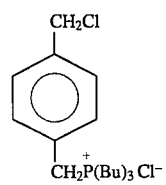

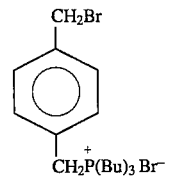

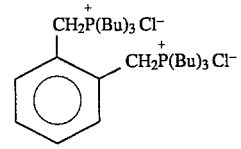

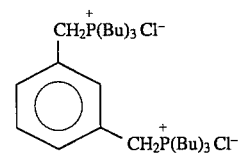

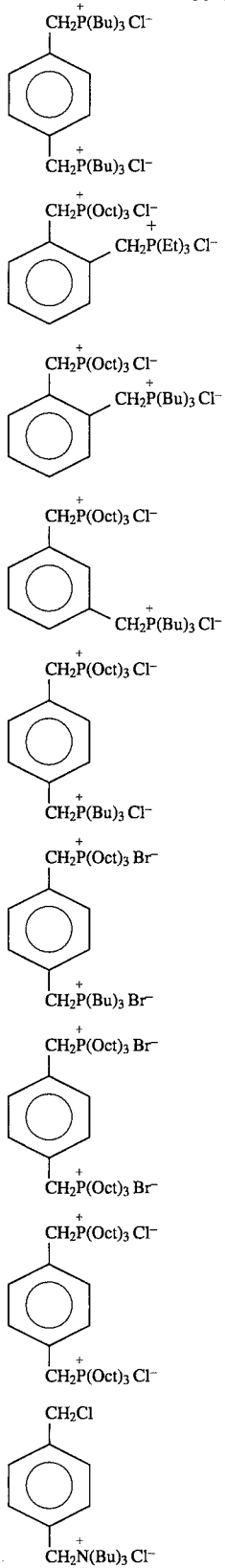
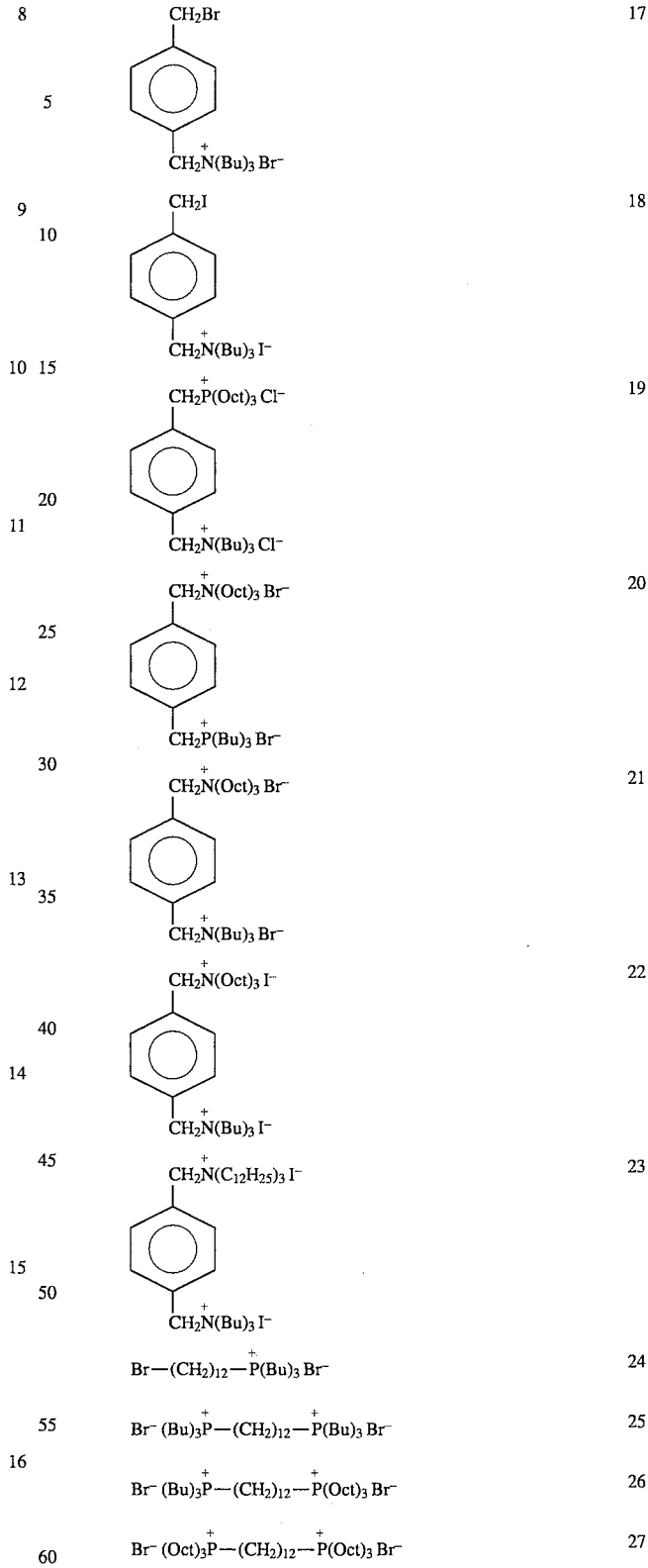
2. Characterization of Surfactants—Surface Tension Lowering Measurement Dicationic surfactant compounds 11–13, 19, 25 and the monocationic surfactant cetyltrimethylammonium bromide (CTAB) were evaluated by the du Nuoy ring surface tension lowering method. Solutions of 1%, 0.1% and 0.0% by weight were measured and the results compared to the surface tension of pure water. A lowering of surface tension is evidence of surfactant properties. Table 1 lists the surface tension γ in dynes/cm for aqueous solutions of several surfactant compounds.

TABLE 1

| Surfactant | 0.01% | 0.1% | 1.0% |
| --- | --- | --- | --- |
| CTAB | 51 | 38 | 31 |
| 11 | 56 | 39 | 27 |
| 12 | 44 | 29 | 29 |
| 13 | 61 | 47 | 30 |
| 19 | 41 | 29 | 26 |
| 25 | 62 | 53 | 41 |

The surface tension of deionized water at 25° C. is 71.97 dynes/cm.

3. Chemiluminescence and Fluorescence Spectra

Chemiluminescence and fluorescence spectra were measured using a Fluorolog II fluorimeter (Spex Ind., Edison, N.J.) with 1 cm quartz cuvettes. All measurements were performed at ambient temperature. A 2 mL solution of LUMIGEN PPD in 221 buffer (0.2M, pH 9.6) containing 0.88 mM $MgCl_2$ and 0.2% surfactant 12 was placed in a cuvette and chemiluminescence initiated by injection of 5 μL of a solution of alkaline phosphatase (Biozyme Laboratories). Scanning the spectrum when the light intensity reached a constant level showed that chemiluminescence emission was maximal at 470 nm.

4. Determination of Optimum Enhancer Concentration in Enzyme Assay

To each of three wells in a 96-well microplate was added 100 μL of a 0.33 mM solution of LUMIGEN PPD in 0.2M 2-methyl-2-amino-1-propanol (221) buffer, pH 9.6 with 0.88 mM $MgCl_2$ and various concentrations of surfactant 12 in the range of 1.0 to 0.01 mg/mL. The plate was incubated at 37° C. and chemiluminescence emission initiated by addition of $9.2 \times 10^{-18}$ mol of calf intestinal alkaline phosphatase. Luminescence was measured for two hours in a Luminoskan luminometer. Maximum luminescence intensity values shown are the average of six wells (FIG. 1). Luminescence from corresponding bank solutions without enzyme is essentially constant throughout the set of solutions. Light intensity and signal-to-background are optimum at a surfactant concentration of 0.5–0.6 mg/mL.

5. Linearity of Detection of Alkaline Phosphatase with LUMIGEN® PPD Enhancer

Figure 2:
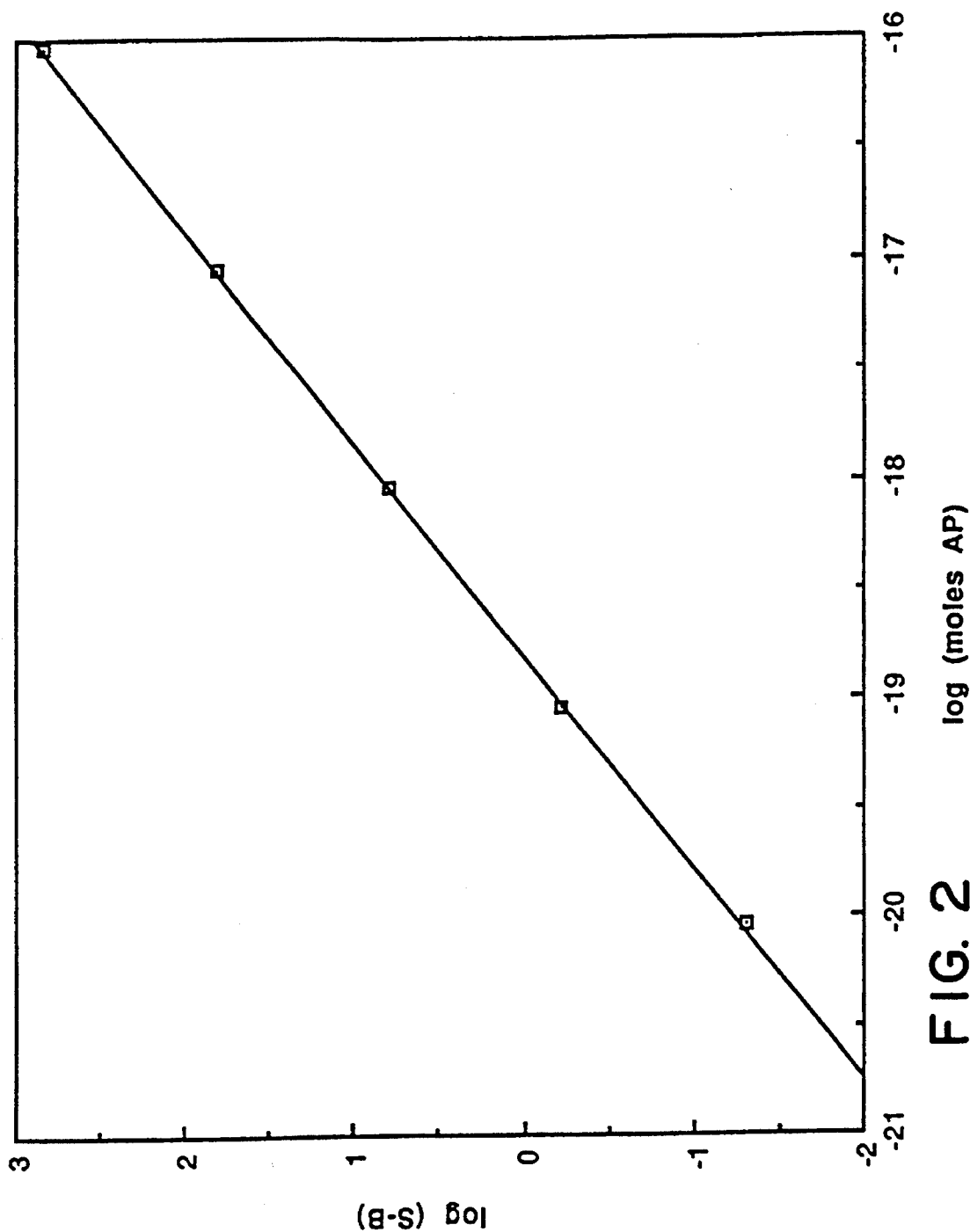
FIG. 2 is a graph of maximum chemiluminescence intensity emitted by 100 μL of a 0.33 mM solution of LUMIGEN PPD in 0.2M 2-methyl-2-amino-1-propanol (221) buffer, pH 9.6 with 0.88 mM $MgCl_2$ and 0.5 mg/mL surfactant 12. Chemiluminescence emission was initiated at 37° C. by addition of 10 μL of dilutions of calf intestinal alkaline phosphatase containing between $9.2 \times 10^{-18}$ mol/ μL and $9.2 \times 10^{-23}$ mol/μL. The graph shows that 0.009 attomol of alkaline phosphatase can be detected.

To each of six wells in a 96-well microplate was added 100 μL of a 0.33 mM solution of LUMIGEN PPD in 0.2M 2-methyl-2-amino-1-propanol (221) buffer, pH 9.6 with 0.88 $MgCl_2$ and 0.5 mg/mL surfactant 12. The plate was incubated at 37° C. and chemiluminescence emission initiated by addition of 10 μL of dilutions of calf intestinal alkaline phosphatase containing between $9.2 \times 10^{-18}$ mol/μL and $9.2 \times 10^{-23}$ mol/μL. FIG. 2 shows that 0.009 amol of alkaline phosphatase can be detected. This represents a 2000-fold lowering of the limit of detection compared to the same system without surfactant (data not shown).

6. Enhancement of the Enzymatically Triggered Decomposition of LUMIGEN PPD.

Table 2 compares the chemiluminescence intensity produced by the decomposition of 100 μL of a 0.33 mM solution of LUMIGEN PPD in 0.2M 221 buffer, pH 9.6, 0.88 mM $MgCl_2$ plus 1.0 mg/mL enhancer when triggered at 37° C. by addition of 5 amol of alkaline phosphatase (AP) in water. Luminescence was measured for two hours in Luminoskan luminometer and the light intensity signal at 30 min was recorded (S). Values shown are the average of six results. Background intensity (B) is the light level in the absence of enzyme. The term S/B is the ratio of the light intensity at 30 min (S) to the background light intensity (B). The entry 'CTAB (0.41 mg/mL)' represents LUMI-PHOS 480 (Lumigen, Inc., Southfield, Mich.).

TABLE 2

Enhancement of Chemiluminescence From alkaline Phosphatase-Triggering of LUMIGEN PPD at 37° C.

| Surfactant | B | S @ 30 min $9 \times 10^{-19}$ mol AP | S/B |
| --- | --- | --- | --- |
| None | 0.135 | 0.731 | 5.43 |
| CTAB (0.41 mg/mL) | 0.085 | 1.834 | 21.65 |
| 6 | 0.124 | 0.588 | 4.73 |
| 7 | 0.123 | 0.619 | 5.05 |
| 10* | 0.342 | 101.3 | 296.6 |
| 11 | 0.229 | 79.8 | 348.3 |
| 12 | 0.157 | 45.7 | 292.0 |
| 13* | 0.222 | 101.2 | 456.7 |
| 19 | 0.145 | 36.35 | 250.3 |
| 25 | 0.125 | 0.814 | 6.54 |
| 26* | 0.247 | 59.1 | 238.9 |
| 27* | 0.399 | 97.24 | 243.8 |

*Solution also contained 5% ethanol. Separately, the addition of 5% ethanol to a solution of LUMIGEN PPD itself in buffer caused no enhancement.

7. Application of Surfactants to the Chemiluminescent Detection of Protein by Western Blotting.

The advantage of compositions of the present invention for the chemiluminescent detection of proteins by the technique of Western blotting is demonstrated in the following example. The sensitivity of detection reagents for Western blotting containing dicationic surfactants was determined using transferrin in known quantities.

Procedure

Rabbit anti-goat IgG-alkaline phosphatase conjugate was obtained from Cappel Products (Durham, N.C.). Human transferrin and fractionated goat anti-human transferrin serum were purchased from Sigma Chemical Co. The IgG sample was centrifuged at 10,000 g for two minutes and the supernatant was used in the immunological reaction.

SDS-PAGE was performed utilizing the buffer system described by Laemmli (U. K. Laemmli, Nature (London), 227, 680 (1970)). The stacking gel was 4.38% acrylamide: 0.12% bisacrylamide. The separating gel was 6.81% acrylamide: 0.19% bisacrylamide. Following electrophoresis, the gel was equilibrated for 7–8 min with the transfer buffer which contained 20 mM Tris, 153 mM glycine and 20% (v/v) methanol. The gel, sandwiched between a sheet of Immobilon-P transfer membrane (Millipore Corp., Bedford, Mass.) and a sheet of chromatography paper 3MM (Whatman), was placed in the transfer unit (Bio-Rad Laboratories, Richmond, Calif). The proteins in the gel were electroeluted for 50–60 min at 4° C. at a 100 V constant voltage. The membrane was then placed in 50 mM Tris-HCl buffered saline at pH 7.4 (TBS) at 4° C. overnight. After this period the membrane was washed with TBS for 15 min.

The membrane was treated with 0.05% Tween-20 in 50 mM Tris-HCl buffered saline at pH 7.4 (T-TBS) containing 1% non-fat powdered milk (NFM) for 1 h at room temperature. This blocked membrane was incubated for 75 min at room temperature with primary antibody (1:500 dilution of goat anti-human transferrin IgG fraction) using T-TBS containing 1% NFM. The membrane was then rinsed a d washed three times for 10 min each with T-TBS at room temperature. The washed membrane was incubated for 1 h at room temperature with secondary antibody (1:5000 dilution of rabbit anti-goat IgG-alkaline phosphatase conjugate) using T-TBS containing 1% NFM. The membrane was rinsed and washed four times for 10 min each with T-TBS followed by a 10 min wash with TBS. The washed membrane was incubated in detection reagent, drained and placed between sheets of transparency film. Kodak (Rochester, N.Y.) X-OMAT-AR X-ray film was exported to the membrane for 5 to 30 sec and developed.

It has been shown that transferrin is not visible in a control blot using normal goat serum in place of the fractionated goat anti-human transferrin serum, These results indicated that the bands detected in the experiments using anti-transferrin serum were immunologically specific. The rapid detection made it possible to make several exposures of the membrane over several hours to optimize image intensity.

Chemiluminescent detection of Western blotted human transferrin utilizing a reagent containing a surfactant enhancer of this invention (A) and LUMI-PHOS 530 (Lumigen, Inc., Southfield, Mich.) (B) was performed. The composition of the former detection reagent solution was LUMI-GEN PPD, 0.33 mM; 2-amino-2-methyl-1-propanol buffer, 0.1M, pH 9.6; $Mg^{2+}$, 0.88 mM; surfactant 12, 1 mg/mL.

Figure 3A:
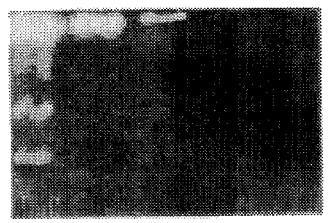
FIGS. 3A and 3B are drawings of Western blot films showing chemiluminescent detection of Western blotted human transferrin on PVDF using goat anti-human transferrin serum, rabbit anti-goat IgG-alkaline phosphatase and a reagent of the present invention in FIG. 3A (LUMIGEN PPD, 0.33 mM, 2-amino-2-methyl-1-propanol buffer, 0.1M, pH 9.6; $Mg^{2+}$, 0.88 mM; surfactant 12, 1 mg/ml) or the reagent LUMI-PHOS 530 consisting of LUMIGEN PPD (0.33 mM) in 0.75M 2-amino-2-methyl-1-propanol buffer, H 9.6, $MgCl_2$ (0.88 mM), CTAB (1.13 mM) and tetradecanolyamino-fluorescein (37.5 μM), (Lumigen, Inc., Southfield, MI) in FIG. 3B. Human transferrin loaded in each slot was (1) 5000 pg, (2) 1000 pg, (3) 200 pg, (4) 50 pg and (5) 20 pg. The transferrin standards utilized are detectable down to 20 pg/slot after a 45 min incubation and 5 sec exposure to X-ray film utilizing a reagent of the present invention (FIG. 3A) and a 60 min incubation and 30 min exposure with Lumi-Phos 530 (FIG. 3B).
Figure 3B:
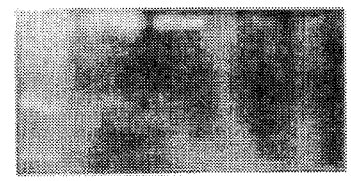

The transferrin standards utilized were detectable down to 20 pg/slot after a 45 min incubation and 5 sec exposure to X-ray film utilizing reagent A (FIG. 3A) and a 60 min incubation and 30 min exposure with LUMI-PHOS 530 (FIG. 3B).

8. Application of Surfactants to the Chemiluminescent Detection of DNA by Southern Blotting.

The advantage of compositions of the present invention for the chemiluminescent detection of DNA on nylon membranes by the technique of Southern blotting is demonstrated in the following example.

Procedure

Avidin-alkaline phosphatase conjugate was obtained from Cappel™ Products (Durham, N.C.). Bovine serum albumin (heat shocked) was purchased from Sigma Chemical Co. (St. Louis, Mo.), Mouse genomic DNA and v-mos DNA were from Clontech (Palo Alto, Calif.). Biotinylated lam a DNA/HindIII fragments, biotin-7-dATP and the Nick Translation kit were from Life Technologies, restriction endonuclease EcoRI was from Boehringer-Mannheim (Indianapolis, Ind.). Nylon transfer membrane was obtained from Micron Separations Inc. (Bedford, Mass.) and nitrocellulose membrane from Schleicher & Schuell Inc. (Keene, N.H.). Kodak X-OMAT AR X-ray film (Rochester, N.Y.) was used in the assay procedure.

Mouse genomic DNA (15 g) was cleaved with EcoRI to completion and divided into 10 µg and 5 µg portions. Restricted DNA was purified by phenol/chloroform extraction and ethanol precipitation. Purified DNA was separated by electrophoresis on 0.77% agarose gel with 40 mmol/L Tris-acetate, 2 mmol/L EDTA, pH 8.0 as the elution buffer. Following electrophoresis, the gel was rinsed with water, equilibrated for 12 min with 0.25 mol/L HCl, rinsed with water again, incubated in 0.5 mol/L NaOH, 1.5 mol/L NaCl for 15 min then in a fresh change of the same solution for 30 min, rinsed with water, and incubated in three changes of 1 mol/L tris, 1.5 mol/L NaCl , pH 7.5 for 15 min each.

Nylon membrane was soaked sequentially with water for two min and 10×SSC for 5 min. DNA was transferred to the membrane by capillary blotting overnight in 10×SSC. The membrane was washed by gentle agitation in 10×SSC for 10 min at room temperature and air-dried on Whatman 3MM blotting paper for 30 min and baked at 80° C. under vacuum for 2 h.

The membrane was soaked in 6X SSPE (20×SSPE is 3 mol/L NaCl, 0.2 mol/L sodium dihydrogen phosphate, 20 mmol/L EDTA, pH 7.4) followed by prehybridization for 3 h at 42° C. in pre-hybridization solution: 6×SSPE, 50% freshly deionized formamide, filtered 5×Denhardt's solution (50×is 1% Ficoll, 1% PVP, 1% BSA (initial fraction by heat shock), filtered 1% SDS and 200 µg/mL sheared, denatured herring sperm DNA. The hybridization probe, v-mos DNA was labeled with biotin-7-dATP by nick translation according to the manufacturers instructions. Genomic DNA was hybridized overnight at 42° C. in 6×SSPE, 45% formamide, filtered 5×Denhardt's, 1% SDS, 200 µg/mL herring sperm DNA with 300 µg/mL denatured biotinylated probe. The biotinylated probe was denatured by boiling 4 min and cooling 10 min at 0° C. The membrane was washed twice with 0.5×SSC, 0.4% SDS at 25° C. for 5 min, three times with 0.5×SSC, 0.4% SDS at 55° C. for 10 min, twice with 2 X SSC at 25° C. for 5 min, twice with TBS (50 mmol/L Tris-HCl, pH 7.4, 0.15 mol/L NaCl) for 3 min. After the wash step, the membrane was blocked at 63° C. for 1 h in filtered 3% BSA, 100 mmol/L Tris-HCl, pH 7.4 0.15 mol/L NaCl and washed in T-TBS (0.05% Tween 20 in TBS) for 3 min.

The blocked membrane was incubated with a 1:2000 dilution of avidin-alkaline phosphatase in T-TBS for 12 min followed by four fresh changes of T-TBS for 5, 15, 15 and 20 min followed by a final wash with TBS for 5 min. Excess buffer was drained off and blots soaked in either the detection reagent A described in Example 7 or LUMI-PHOS 530 detection reagent for 10 min. Excess reagent was drained off, and the blots placed between transparent sheets and exposed to X-ray film.

Figure 4A:
FIGS. 4A and 4 B are drawings of Southern blot films showing chemiluminescent detection of Southern blotted single copy gene from mouse genomic DNA on nylon membrane using biotinylated v-mos probe and avidin-alkaline phosphatase. Incubations and exposures were.
Figure 4B:

The single copy gene corresponding to the homologous gene of v-mos was detected at 14 kbp by soaking the membrane with detection reagent and exposure to Kodak XAR-5 film for varying lengths of time. After an incubation period of 35 min, a band corresponding to the single copy gene in both fractions was visible with a 25 minute exposure to film using reagent A of the present invention (FIG. 4A). Shorter incubation times also produced excellent images. Multiple exposures could be easily performed for more than a day. Comparable sensitivity using LUMI-PHOS 530 (FIG. 4B) required a longer exposure of 100 min after a 60 min incubation.

9. Chemiluminescent Detection of DNA on Nitrocellulose Membrane.

Compositions of the present invention are especially useful for the chemiluminescent detection of DNA on nitrocellulose membranes by the technique of Southern blotting as is demonstrated in the following example.

Figure 5A:
FIGS. 5A and 5B are drawings of Southern blot films showing chemiluminescent detection of single copy gene from mouse genomic DNA on nitrocellulose membrane using biotinylated v-mos probe, avidin-alkaline phosphatase, a reagent of the present invention as used for FIG. 3A (FIG. 5A) and LUMI-PHOS 530 (FIG. 5B). Incubations and exposures were: 40 min and 60 min (FIG. 5A) and 3 h and 16 h (FIG. 5B). Column 1 is 40 ng biotinylated lambda DNA/HindIII fragments. Column 2 and 3 are 10 and 5 μg EcoRI-restricted mouse genomic DNA, respectively.
Figure 5B:

The Southern blot analysis of EcoRI restricted mouse DNA was also performed with 10 and 5 g samples blotted onto nitrocellulose using the procedure described in the preceding example with one modification. Prior to transfer, nitrocellulose membrane was soaked sequentially with water for 2 min and 10×SSC for 30 min. Transfer, washing, blocking and hybridization steps were conducted as described above. The single copy gene was detected after a 40 min incubation in reagent A described in Example 7 with a 60 min exposure to XAR-5 film (FIG. 5A). Membrane soaked in LUMI-PHOS 530 required a longer 3 h incubation and overnight exposure (FIG. 5B).

10. Application of Surfactants to the Chemiluminescent Southern Blotting by Pre-treatment of Membranes.

Southern blot analyses of mouse genomic DNA were also performed with a modified chemiluminescent detection procedure in which the nylon or nitrocellulose detection membrane is first treated with a solution of the dicationic surfactant enhancer substance prior to addition of detection reagent. This process provides a more intense signal than that resulting from simply contacting the membrane with the detection reagent for equivalent incubation and exposure times. Thus incubation and exposure times may be decreased to achieve equal sensitivity.

In a Southern blot analysis performed as described in Examples 8 and 9, after the final wash step but before contacting the membrane with the detection reagent, the membrane was briefly blotted on filter paper to remove excess buffer. The membrane was placed in a solution consisting of 0.1M 2-amino-2-methyl-1-propanol buffer, pH 9.6 containing 0.88 mM $Mg^{2+}$ and 1 mg/mL of surfactant 12 and soaked for 10 min. The membrane was removed from the solution, blotted on filter paper and placed in detection reagent A solution described in Example 7 for incubation for 1.5–2 hours. The membrane which was treated with surfactant enhancer solution prior to treatment with detection reagent A achieved equal signal intensities 3–4 times faster than the membrane which was not pre-treated.

It is intended that the foregoing description be only illustrative of the present invention and that the present invention be limited only by the hereinafter appended claims.

We claim

1. A composition which comprises:
   (a) a light producing molecule which is activatable to produce chemiluminescence; and
   (b) an enhancer which is a compound which comprises:

$$X^-(R_1)_3A^+CH_2\text{---Link---}CH_2A^+(R_2)^3X^-$$

wherein each of A is selected independently from the group consisting of phosphorus and nitrogen atoms, wherein X is an anionic counterion, $R_1$ and $R_2$ are selected from the group consisting of alkyl and aralkyl groups containing up to 20 carbon atoms and $R_1$, and $R_2$ are different, and wherein Link is a carbon chain group selected from the group consisting of dialkylenearyl, aryl, alkylene, alkenylene and alkynylene groups containing 4 to 20 carbon atoms.

2. A composition which comprises:
   (a) a stable 1,2-dioxetane; and
   (b) an enhancer compound which is a compound which comprises:

$$X^-(R_1)_3A^+CH_2\text{---Link---}CH_2A^+(R_2)_3X^-$$

wherein each of A is selected independently from the group consisting of P and N, wherein X is a halide anion selected from the group consisting of fluoro, iodo, bromo and chloro and $R_1$ and $R_2$ are selected from the group consisting of alkyl and aralkyl groups containing up to 20 carbon atoms $R_1$ and $R_2$ are different, and wherein Link is a carbon chain group selected from the group consisting of dialkylenearyl, arylene, alkylene, alkenylene and alkynylene groups containing 4 to 20 carbon atoms, wherein enhanced chemiluminescence is produced in a solution or on a surface in the presence of a sufficient quantity of the enhancer compound compared to the chemiluminescence obtained in the absence of the enhancer compound.

3. The composition of claim 2 wherein the 1,2-dioxetane is of the formula:

wherein $R_5$ and $R_6$ are organic groups which can be combined together to form a spiro-fused cyclic or polycyclic ring alkyl group containing 6 to 30 carbon atoms which can additionally contain heteroatoms, wherein $R_3$ is a group selected from alkyl and aralkyl groups containing up to 20 carbon atoms and wherein $R_4$ is an aryl group substituted with a Y-oxy group which forms an unstable oxide intermediate dioxetane when triggered to remove a chemically labile group Y by an activating agent selected from the group consisting of acids, bases, salts, enzymes, inorganic and organic catalysts and electron donors.

4. The composition of claim 2 wherein the 1,2-dioxetane is of the formula:

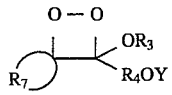

wherein $R_3$ is selected from the group consisting of alkyl and aralkyl groups containing up to 8 carbon atoms and can additionally contain heteroatoms, wherein

is selected from the group consisting of spirofused cyclic and polycyclic ring alkyl groups containing 6 to 30 carbon atoms and can additionally contain heteroatoms, wherein $R_4$ is selected from the group consisting of aryl, biaryl, heteroaryl, fused ring polycyclic aryl and fused ring polycyclic heteroaryl groups and wherein OY is a Y-oxy group which forms an unstable oxide intermediate dioxetane compound when triggered to remove a chemically labile group Y by an activating agent selected from the group consisting of acids, bases, salts, enzymes, inorganic and organic catalysts and electron donors.

5. The composition of claim 4 wherein the OY group is selected from the group consisting hydroxyl, trialkylsilyloxy, triarylsilyloxy, inorganic oxy acid salt, phosphate salt, sulfate salt, oxygen-pyranoside, aryl carboxyl esters and alkyl carboxyl esters.

6. The composition of claim 5 wherein the OY group is $OPO_3Na_2$.

7. The composition of claim 5 wherein

is selected from the group consisting of adamantyl and substituted adamantyl groups.

8. The composition of claim 6 wherein $R_4$ is meta-phenyl.

9. The composition of claim 6 wherein $R_3$ is methyl.

10. The composition of claim 7 wherein $R_3$ is methyl, wherein $R_4$ is meta-phenyl, wherein OY is a phosphate salt and wherein the activating agent is alkaline phosphatase.

11. The composition of claim 10 wherein the OY phosphate salt is $OPO_3Na_2$.

12. The composition of any of claims 1, 2, 3, 4, 5, 6, 7, 8, 9, 10 or 11 wherein both A are phosphorous atoms and wherein Link is selected from the group consisting of ortho-, meta- and para-phenylene groups.

13. The composition of any of claims 1, 2, 3, 4, 5, 6, 7, 8, 9, 10 or 11 wherein both A are nitrogen atoms and wherein Link is selected from the group consisting of ortho-, meta-, and para-phenylene groups.

14. The composition of any of claims 1, 2, 3, 4, 5, 6, 7, 8, 9, 10 or 11 wherein one A is a phosphorus atom and the other A is a nitrogen atom and wherein Link is selected from the group consisting of ortho-, meta- or para-phenylene groups.

* * * * *

UNITED STATES PATENT AND TRADEMARK OFFICE
CERTIFICATE OF CORRECTION

PATENT NO. : 5,484,556

DATED : January 16, 1996

INVENTOR(S) : M. Hashem Akhavan-Tafti and Zahra Arghavani

It is certified that error appears in the above-identified patent and that said Letters Patent is hereby corrected as shown below:

Column 2, line 59, "Hanaley" should read --Handley--.

Column 5, line 48, ", H 9.6" should read --, pH 9.6--.

Column 6, line 18, "-Link-$CH_2A^+(R_2)_3X$_" should read -- -Link-$CH_2A^+(R_2)_3X^-$ --.

Column 6, line 40, "-Link-$CH_2A^+(R_2)_3X$_" should read -- -Link-$CH_2A^+(R_2)_3X^-$ --.

Column 7, line 1, "with P and wherein P" should read --with $R_4$ and wherein $R_4$--.

Column 7, line 24, after "wherein" and before "represents", -- $R_4$ -- should be inserted.

Column 7, line 57, after "wherein", -- $R_4$ -- should be inserted.

Column 8, line 44, "-Link-$CH_2A^+(R_2)_3X$_" should read -- -Link-$CH_2A^+(R_2)_3X^-$ --.

Column 9, line 57&58, "DNA or A probes" should read --DNA or RNA probes--.

Column 13, line 2, "(dt, 9)" should read --(dt, 9H)--.

UNITED STATES PATENT AND TRADEMARK OFFICE
CERTIFICATE OF CORRECTION

PATENT NO.  : 5,484,556
DATED       : January 16, 1996
INVENTOR(S) : M. Hashem Akhavan-Tafti and Zahra Arghavani It is certified that error appears in the above—identified patent and that said Letters Patent is hereby corrected as shown below:

Column 13, line 37, "69.8" should read --69.2--.

Column 14, line 42, "2.4" should read --2.48--.

Column 15, line 6, "7.5 - 7.6" should read --7.51 - 7.61--.

Column 15, line 24, "-4-tri-n-" should read -- -4-(tri-n- --.

Column 15, lines 37 and 38, "4.36 4.41" should read --4.36 - 4.41 --.

Column 16, line 29, "-4-tri-n" should read -- -4-(tri-n --.

Column 16, line 39, "(m, 8H)" should read --(m, 48H)--.

Column 16, line 55, "dibromide (2L)" should read --dibromide (21)--.

Column 16, line 56, "4-bromo" should read --4-(bromo --.

Column 17, line 8, "(CDCl$_3$) 60.87" should read --(CDCl$_3$) δ 0.87--.

Column 17, line 15, "(2.3 g" should read --(3.3 g--.

Column 17, line 24, "20 (s, 4H)" should read --5.20 (s, 4H)--.

Column 18, line 3, "pressure o give" should read --pressure to give--.

UNITED STATES PATENT AND TRADEMARK OFFICE
CERTIFICATE OF CORRECTION

PATENT NO. : 5,484,556
DATED : January 16, 1996
INVENTOR(S) : M. Hashem Akhavan-Tafti and Zahra Arghavani It is certified that error appears in the above—identified patent and that said Letters Patent is hereby corrected as shown below:

Column 18, line 6, after "(m, 16H)." a new paragraph should begin.

Column 21, line 27, "0.2%" should read --0.1%--.

Column 21, line 44, "bank" should read --blank--.

Column 21, line 57, "10$^-$23" should read --$10^{-23}$--.

Column 22, line 66, "ad" should read --and--.

Column 23, line 9, "exported" should read --exposed--.

Column 23, line 49, "(15 g)" should read --(15 µg)--.

UNITED STATES PATENT AND TRADEMARK OFFICE
CERTIFICATE OF CORRECTION

PATENT NO. : 5,484,556
DATED : January 16, 1996
INVENTOR(S) : M. Hashem Akhavan-Tafti and Zahra Arghavani It is certified that error appears in the above—identified patent and that said Letters Patent is hereby corrected as shown below:

Column 24, line 50, "5 g" should read --5 $\mu$g--.

Column 25, line 27, "-Link-$CH_2A^+(R_2)^3X^-$" should read -- -Link-$CH_2A^+(R_2)_3X^-$ --.

Column 26, line 35 (Claim 41), after "consisting" and before "hydroxyl", --of-- should be inserted.

Signed and Sealed this

Twenty-fifth Day of June, 1996

BRUCE LEHMAN

Attest:

Attesting Officer   Commissioner of Patents and Trademarks